United States Patent
Söderlund et al.

(10) Patent No.: US 11,906,531 B2
(45) Date of Patent: Feb. 20, 2024

(54) METHOD OF DETECTING THE PRESENCE OF A BIOMARKER IN A SAMPLE OF A FLOWABLE SUBSTANCE, A DETECTOR ASSEMBLY FOR USE IN THE DETECTION OF A BIOMARKER IN A SAMPLE OF A FLOWABLE SUBSTANCE AND A DETECTOR UNIT FOR USE IN THE DETECTION OF THE PRESENCE OF A BIOMARKER IN A SAMPLE OF A FLOWABLE SUBSTANCE

(71) Applicant: Calmark Sweden AB, Karlstad (SE)

(72) Inventors: Anna Söderlund, Arsta (SE); Tania Correia, Stockholm (SE); Anders Abjörnsson, Helsingborg (SE); Johan Svahn, Lärbro (SE); Catarina Moreira Pinho, Bromma (SE); Ana Catarina De Araújo Silva, Nacka (SE); Michael Lundh, Lund (SE)

(73) Assignee: CALMARK SWEDEN AB, Karlstad (SE)

( * ) Notice: Subject to any disclaimer, the term of this patent is extended or adjusted under 35 U.S.C. 154(b) by 645 days.

(21) Appl. No.: 17/254,609

(22) PCT Filed: Jun. 27, 2019

(86) PCT No.: PCT/EP2019/067198
§ 371 (c)(1),
(2) Date: Dec. 21, 2020

(87) PCT Pub. No.: WO2020/011552
PCT Pub. Date: Jan. 16, 2020

(65) Prior Publication Data
US 2021/0270850 A1    Sep. 2, 2021

(30) Foreign Application Priority Data

Jul. 10, 2018 (SE) .................................. 1850879-6
Jul. 10, 2018 (SE) .................................. 1850880-4

(51) Int. Cl.
*G01N 33/68* (2006.01)
*G01N 21/33* (2006.01)
(Continued)

(52) U.S. Cl.
CPC ...... *G01N 33/726* (2013.01); *B01L 3/502715* (2013.01); *B01L 2200/06* (2013.01); *B01L 2300/027* (2013.01)

(58) Field of Classification Search
CPC .............. G01N 33/726; G01N 33/68; B01L 3/502715; B01L 2200/06; B01L 2300/027
See application file for complete search history.

(56) References Cited

U.S. PATENT DOCUMENTS 4,761,381 A    8/1988 Blatt et al.
5,147,606 A    9/1992 Charlton et al.
(Continued)

FOREIGN PATENT DOCUMENTS

EP    2875866 A1    5/2015
WO    WO-00/70350 A1    11/2000
(Continued)

OTHER PUBLICATIONS

International Searching Authority, International Search Report and Written Opinion for International Application No. PCT/EP2019/067198, dated Nov. 11, 2019, (13 pages), European Patent Office, Rijswijk, Netherlands.

*Primary Examiner* — Jennifer Wecker
*Assistant Examiner* — Oyeleye Alexander Alabi
(74) *Attorney, Agent, or Firm* — Alston & Bird LLP

(57) ABSTRACT

A detector assembly and method of detecting the presence of a biomarker, such as bilirubin, in a sample of a flowable substance and a detector unit (1) are disclosed. The method comprises providing a receiver body (2) shaped to define a receiving chamber (3). The receiving chamber (3) has an
(Continued)

outlet opening (5) through which a flowable substance can leave the receiving chamber (3). The receiving chamber (3) has a maximum capacity for holding a volume of the flowable substance. A quantity of the flowable substance is supplied to the receiving chamber (3) and caused to pass through the outlet opening. The receiver body (2) can move relative to a guide (10) of the receive body (2) from a first position in which the outlet opening (5) is blocked to a second position in which the outlet opening (5) is not blocked. In the second position, a metered quantity of flowable substance in the receiving chamber (3) can leave the receiving chamber (3).

20 Claims, 7 Drawing Sheets

(51) Int. Cl.
- *G01N 21/64* (2006.01)
- *G01N 33/52* (2006.01)
- *C07C 309/65* (2006.01)
- *C07C 309/73* (2006.01)
- *A01N 1/02* (2006.01)
- *G01N 1/40* (2006.01)
- *G01N 33/543* (2006.01)
- *G01N 33/532* (2006.01)
- *G01N 33/569* (2006.01)
- *G01N 33/72* (2006.01)
- *B01L 3/00* (2006.01)

(56) References Cited

U.S. PATENT DOCUMENTS

| | | |
|---|---|---|
| 9,283,560 B2 | 3/2016 | Dothie |
| 2004/0156037 A1 | 8/2004 | Mawhirt et al. |
| 2006/0222567 A1 | 10/2006 | Kloepfer et al. |
| 2014/0329262 A1 | 11/2014 | Karlsson et al. |
| 2019/0353670 A1* | 11/2019 | Soederlund ............ G01N 33/68 |

FOREIGN PATENT DOCUMENTS

| | | |
|---|---|---|
| WO | WO-03/020424 A1 | 3/2003 |
| WO | WO-2005/086744 A2 | 9/2005 |
| WO | WO-2016/176366 A1 | 11/2016 |
| WO | WO-2018/130506 A1 | 7/2018 |

\* cited by examiner

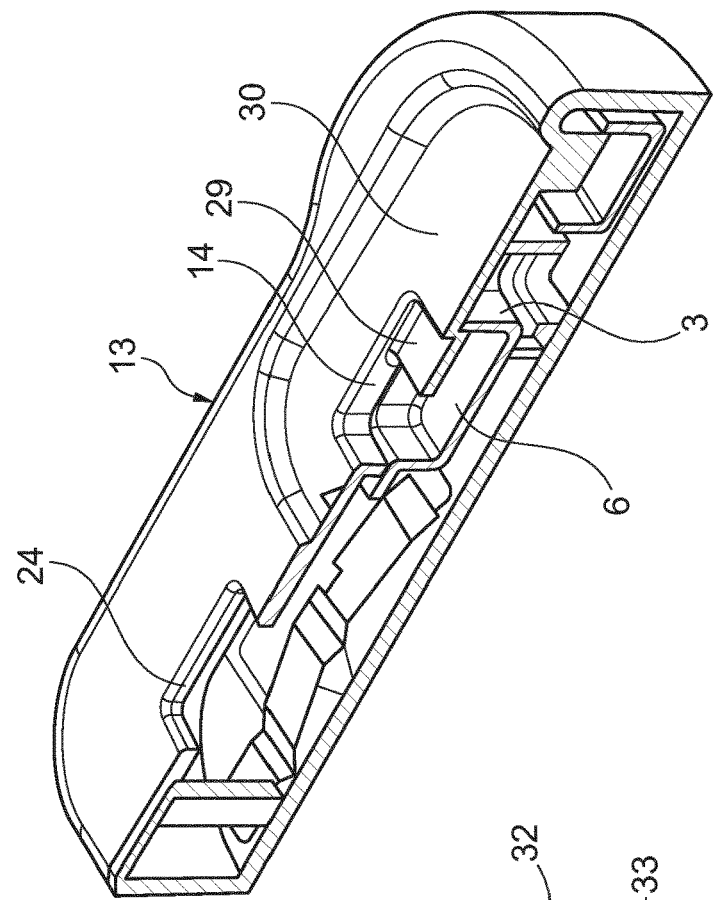
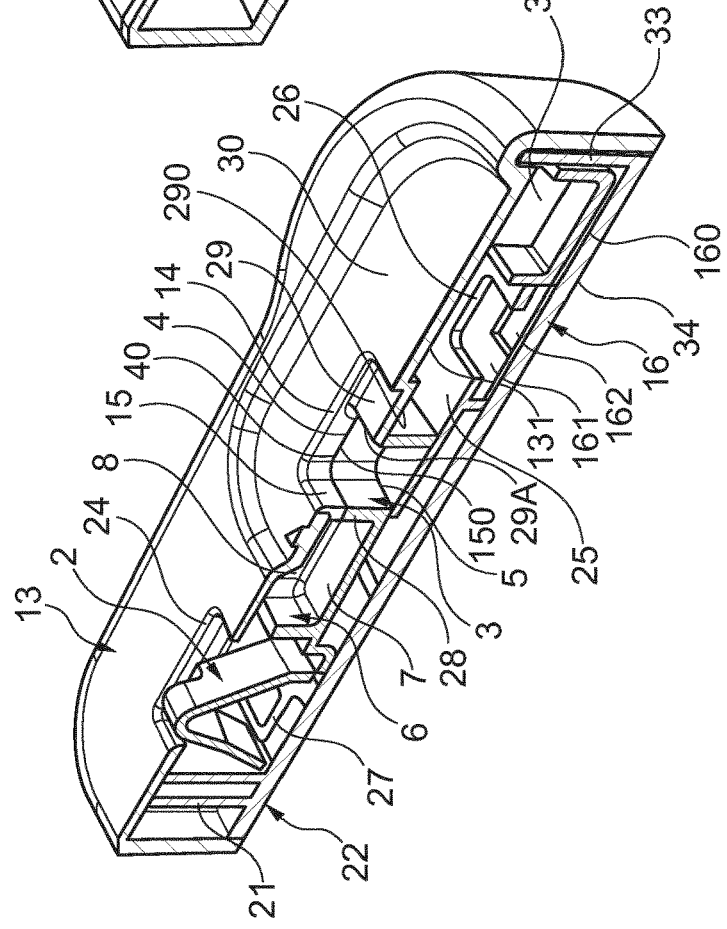

METHOD OF DETECTING THE PRESENCE OF A BIOMARKER IN A SAMPLE OF A FLOWABLE SUBSTANCE, A DETECTOR ASSEMBLY FOR USE IN THE DETECTION OF A BIOMARKER IN A SAMPLE OF A FLOWABLE SUBSTANCE AND A DETECTOR UNIT FOR USE IN THE DETECTION OF THE PRESENCE OF A BIOMARKER IN A SAMPLE OF A FLOWABLE SUBSTANCE

CROSS REFERENCE TO RELATED APPLICATIONS

This application is a National Stage Application, filed under 35 U.S.C. § 371, of International Application No. PCT/EP2019/067198, filed Jun. 27, 2019, which international application claims priority to and the benefit of Swedish Application No. 1850879-6, filed Jul. 10, 2018, and Swedish Application No. 1850880-4, filed Jul. 10, 2018; the contents of all of which as are hereby incorporated by reference in their entireties.

BACKGROUND

Related Field

The present invention relates to a method of detecting the presence of a biomarker, such as bilirubin, in a sample of a flowable substance such as blood. The invention also relates to a detector assembly for use in the detection of a biomarker, such as bilirubin, in a sample of a flowable substance. The invention furthermore relates to a detector unit for use in detection of the presence of a biomarker, such as bilirubin, in a sample of a flowable substance.

Description of Related Art

Rapid methods for analysis of substances such as blood, saliva or urine are desired within the art. U.S. Pat. No. 4,671,381 discloses a volume metering capillary device for applying a flowable substance sample onto a reactive surface. The device according to that patent comprises oppositely disposed top and bottom surface layers defining therebetween a capillary zone of intended flowable substance transport of a test liquid. The capillary zone is divided into a sample test chamber containing interactive material and an overflow chamber for excess test liquid. An overflow channel is located between the sample test chamber and the overflow chamber and functions to permit overflow of test flowable substance from the sample test chamber to the overflow chamber and acts as a capillary lock to break connection between test flowable substance in the sample chamber and test flowable substance in the overflow chamber. The device also has a sample application port which is in communication with the sample test chamber.

U.S. Pat. No. 9,283,560 discloses a passive microfluidic metering device. The device disclosed in that patent has a sample fluid input chamber, a first overspill chamber, a second overspill chamber and a metering conduit in fluid communication with the fluid input chamber and the first overspill chamber. U.S. Pat. No. 5,147,606 discloses a diagnostic device for testing fluids such as blood. The diagnostic device according to that document comprises a housing for holding flowable substance and a sample application port in the housing for introducing a sample of fluid into the housing. Metering chamber means are positioned in the housing and constructed so as to receive the fluid sample via the sample application port. A fluid capillary is positioned in the housing and comprises a first end and a second end and the first end is coupled to the metering chamber means for carrying fluid therefrom to the second end. A reaction compartment means is positioned in the housing and includes a first chamber means with a reagent and a second chamber means disposed between the metering chamber means and the first chamber means and contains a filter therein, the filter being positioned in flow communication with the metering chamber means. The filter is positioned and arranged to allow fluid entering the reaction compartment means from the metering chamber means to be filtered and the reagent to react with the filtered fluid. In the context of such analysis, it is sometimes desirable that the analysis can be performed on a precisely metered quantity of the substance.

It has been suggested in international patent application PCT/EP2018/050424 and Swedish patent application No. 1750028-1 that a method of detecting the presence of a biomarker in a sample of a flowable substance can make use of a disposable sample receiver having a receiving chamber with a bottom outlet and a flow path leading away from the bottom outlet. A reagent is placed within the flow path and the sample is disposed in the receiving chamber. A depression is provided that surrounds the receiving chamber and the receiving chamber is filled until an excess of the flowable substance spills over into the depression. The receiving chamber is then emptied by removing from the bottom outlet a separating member that is impermeable to the flowable substance such that flowable substance can leave the receiving chamber. Since excess substance has spilled over into the depression, a metered quantity of the flowable substance can be obtained. While that method gives good results, surface tension in the flowable substance may still be a source of error. It is an object of the present invention to provide a method of detecting the presence of a biomarker in a sample of the flowable substance that allows a user to obtain a precisely metered quantity of a flowable substance, also taking surface tension in the flowable substance into account.

BRIEF SUMMARY

The invention relates to a method of detecting the presence of a biomarker, such as bilirubin or the like, in a sample of a flowable substance. The inventive method comprises the step of providing a receiver body that is shaped to define a receiving chamber that has an inlet opening through which the flowable substance can enter the receiving chamber. The receiving chamber further has an outlet opening through which a flowable substance can leave the receiving chamber when the outlet opening is not blocked. The receiving chamber has a maximum capacity for holding a volume of the flowable substance when the outlet opening is blocked. A detector is provided and a quantity of the flowable substance is added/supplied to the receiving chamber and caused to pass through the outlet opening and come into contact with the detector. According to the invention, the sample receiver body is shaped to define an overflow chamber that is separated from the receiving chamber. The overflow chamber has a bottom, a circumferential wall and chamber opening such that it can hold a quantity of the flowable substance. A guide for the receiver body is provided which guide is shaped to be capable of cooperating with the receiver body such that the receiver body can be caused to move relative to the guide in a movement from a first position in which the outlet opening is blocked to a second position in which the outlet opening is not blocked, the path of which movement is determined by cooperating surfaces of the guide and the receiver body.

A cover is provided which cover is connected to the guide in such a way that the guide and the cover are in a fixed position relative to each other. The receiver body is in contact with the cover at least when the receiver body is in its first position and the cover is further shaped to define an opening that can be made to at least partially coincide with the inlet opening of the receiving chamber when the receiver body is in the first position and to coincide with the chamber opening of the overflow chamber when the receiver body is in its second position. The opening in the cover is limited by a circumferential wall that forms an extension of the receiving chamber when the receiver body is in its first position such that the receiving chamber and the opening in the cover can cooperate to hold a quantity of the flowable substance that exceeds the maximum capacity of the receiving chamber itself when the receiver body is in its first position. The detector is placed in a position which is adjacent the outlet of the receiving chamber when the receiver body is in its second position such that flowable substance can leave the receiving chamber and come into contact with the detector. The method further comprises pouring/supplying a quantity of the flowable substance into the receiving chamber while the receiver body is in its first position and subsequently causing the receiver body to move from the first position to the second position such that any quantity of the flowable substance that has been delivered to (poured into, supplied to) the receiving chamber and which exceeds the maximum capacity of the receiving chamber itself will be separated from the rest of the flowable substance that has been poured into the receiving chamber and instead enter the overflow chamber whereby the quantity of flowable substance which remains in the receiving chamber will be a metered quantity that is free to leave the receiving chamber and come into contact with the detector.

The movement of the receiver body is preferably a linear movement, but the receiver body and the guide could conceivable be shaped such that the receiver body has a movement that is not linear. For example, the receiver body could be made to move along the guide in a path that has the shape of an arc.

Preferably, the guide is shaped such that the guide blocks the outlet opening of the receiving chamber when the receiver body is in its first position. However, embodiments are conceivable in which it is not a part of the guide that blocks the outlet opening when the receiver body is in its first position.

The movement of the receiver body can be caused by pushing or pressing directly on the receiver body. However, the movement of the receiver body is preferably caused by pressing an activation mechanism operatively connected to the receiver body such that pressing the activation mechanism causes the activation mechanism to act on the receiver body to move it from the first position of the receiver body to the second position of the receiver body.

Preferably, the method works such that gravity is used to cause the flowable substance to leave the receiving chamber through the outlet opening. However, embodiments are conceivable in which separate means for pressing/squeezing the flowable substance out through the outlet opening.

The invention also relates to a detector assembly for use in the detection of a biomarker, such as bilirubin or the like, in a sample of a flowable substance. The inventive detector assembly comprises a receiver body shaped to define a receiving chamber having an inlet opening through which the flowable substance can enter the receiving chamber and an outlet opening through which a flowable substance can leave the receiving chamber when the outlet opening is not blocked. The receiving chamber has a maximum capacity for holding a volume of the flowable substance when the outlet opening is blocked. According to the invention, the sample receiver body is shaped to define an overflow chamber that is separated from the receiving chamber. The overflow chamber has a bottom, a circumferential wall and chamber opening such that flowable substance can enter the overflow chamber through the chamber opening. The detector assembly also comprises a guide for the receiver body which guide is shaped to cooperate with the receiver body such that the receiver body can be caused to move relative to the guide in a movement from a first position in which the outlet opening is blocked to a second position in which the outlet opening is not blocked. The path of the movement is determined by cooperating surfaces of the guide and the receiver body.

The detector assembly further comprises a cover which cover is connected to the guide in such a way that the guide and the cover are in a fixed position relative to each other and the receiver body is in contact with the cover at least when the receiver body is in its first position. The cover is further shaped to define an opening that can be made to at least partially coincide with the inlet opening of the receiving chamber when the receiver body is in the first position and to coincide with the chamber opening of the overflow chamber when the receiver body is in its second position. The opening in the cover is limited by a circumferential wall that forms an extension of the receiving chamber when the receiver body is in its first position such that the receiving chamber and the opening in the cover can cooperate to hold a quantity of the flowable substance that exceeds the maximum capacity of the receiving chamber itself when the receiver body is in its first position.

The detector assembly further comprises a detector which is located in the detector assembly in a position that is adjacent the outlet opening of the receiving chamber when the receiver body is in its second position. As an example, the detector may comprise or hold a reagent that is selected to react with a biomarker. However, it should be understood that the detector assembly may be sold and delivered with a detector that does not comprise or hold any such reagent, for example to allow a user to add to the detector a suitable according to what he or she prefers.

In preferred embodiments, the detector assembly comprises an activation mechanism operatively connected to the guide such that pressing the activation mechanism causes the activation mechanism to act on the receiver body to move it from the first position of the receiver body to the second position of the receiver body.

Preferably, the detector assembly comprises a bottom part and the cover can be shaped such that it can be connected to the bottom part and it can be so shaped that, when connected to each other, they form together a shell in which the guide, the receiver body and the activation mechanism are located. The cover can then be shaped to define an access opening for the activation mechanism such that a user can access the activation mechanism through the access opening and cause the receiver body to move from its first position to its second position. Optionally, the guide can be secured to the bottom part such that the position of the guide is fixed in relation to the bottom part and thereby also in relation to the cover when the cover is connected to the bottom part.

The activation mechanism can take many different forms. In one practical and advantageous embodiment, the activation mechanism comprises a first link and a second link connected to each other by an articulated joint, the first link being secured to a part of the shell and the second link being connected to the receiver body. The first and the second link have such dimensions that they can form a V-shaped protrusion when the receiver body is in its first position. The V-shaped protrusion is then accessible through the access opening such that it can be pressed down by an operator thereby causing the articulated joint to move toward the bottom part and the receiver body to move from its first position to its second position.

Preferably, the guide comprises a plate that blocks the outlet opening of the receiving chamber when the receiver body is in its first position. The plate can then have an opening that coincides with the outlet opening of the receiving chamber when the receiver body is in its second position such that flowable substance can leave the receiving chamber through the outlet opening when the receiver body is in its second position.

The invention also relates to a detector unit for use in detection of the presence of a biomarker, such as bilirubin, in a sample of a flowable substance. The inventive detector unit includes a portable detector housing having a fitting place for reception of a detector assembly. The inventive detector unit further comprises the inventive detector assembly as described above, the detector assembly being adapted to be located in said fitting place and said detector housing comprises an activation device arranged to activate the detector assembly.

The inventive detector unit is designed such that the activation device is movably arranged in relation to said fitting place and arranged to push the activation mechanism of the detector assembly upon simultaneously triggering a detection process within the detector unit.

In preferred embodiments, the detector assembly is arranged with irregularity of its outer configuration and said fitting place is being adapted to said outer configuration to thereby safeguard correct positioning of the detector assembly in the fitting place.

BRIEF DESCRIPTION OF THE DRAWINGS

FIG. 8 is a cross-sectional perspective view, illustrating the inventive detector assembly with the cover connected to the bottom part, when the receiver body is in its first position.

FIG. 9 is a cross-sectional perspective view, illustrating the inventive detector assembly with the cover connected to the bottom part, when the receiver body is in its second position.

DETAILED DESCRIPTION OF VARIOUS EMBODIMENTS

Figure 1:
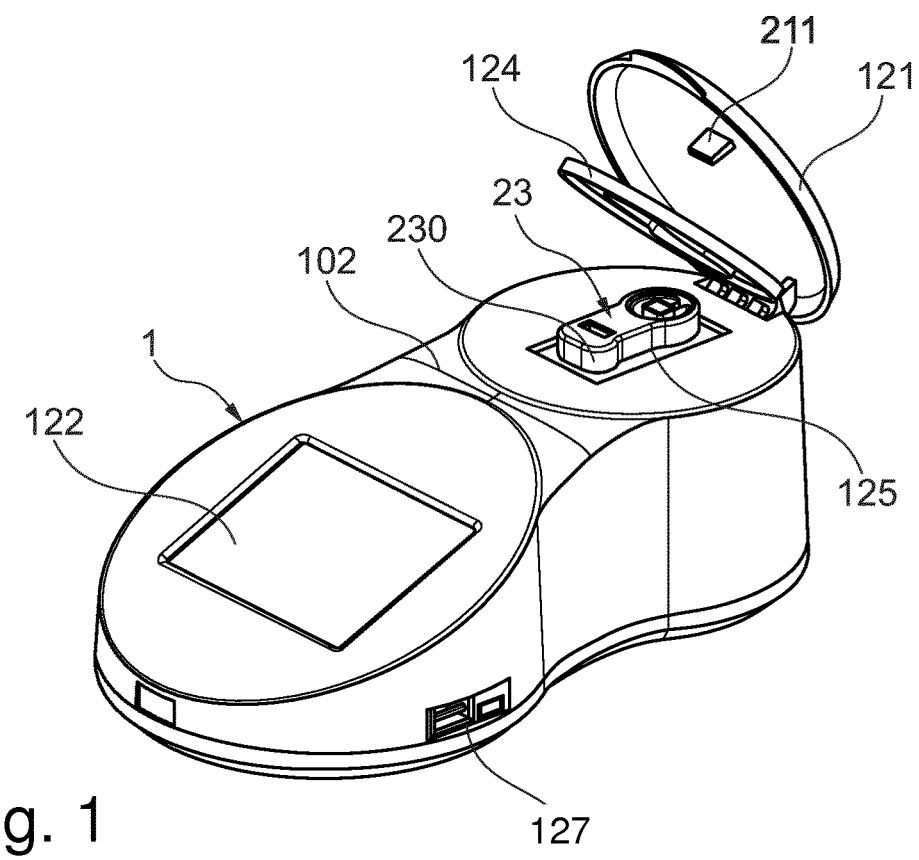
FIG. 1 shows an isometric view of a preferred embodiment of a detector unit of the invention, including a detector housing and a disposable detector assembly.

The detector unit 1 shown in FIG. 1 can advantageously be used in connection with the present invention and is adapted for use in detection of the presence of a biomarker, such as bilirubin, in a sample of a flowable substance, which usually is a body fluid, such as whole blood, urine, and saliva, for example. The unit 1 includes a portable detector housing 102 having a fitting place 125 for reception of a, preferably disposable, detector assembly 23, schematically shown in FIGS. 3, 4 and 5, having a detector device 160 (see FIG. 5). Preferably the fitting place 125 includes a depression or a plurality of protrusions, formed to fit the shape/contour of the detector assembly 23. Further, there is a lid 121 that on shutting will cover the detector assembly 23 and simultaneously activate the detector assembly 23 and also the detection process of the detector unit 1 by means of an activator pin 211, such that every sample to be analyzed may be subjected to the same testing conditions with regard to volume and timing.

Figure 2:
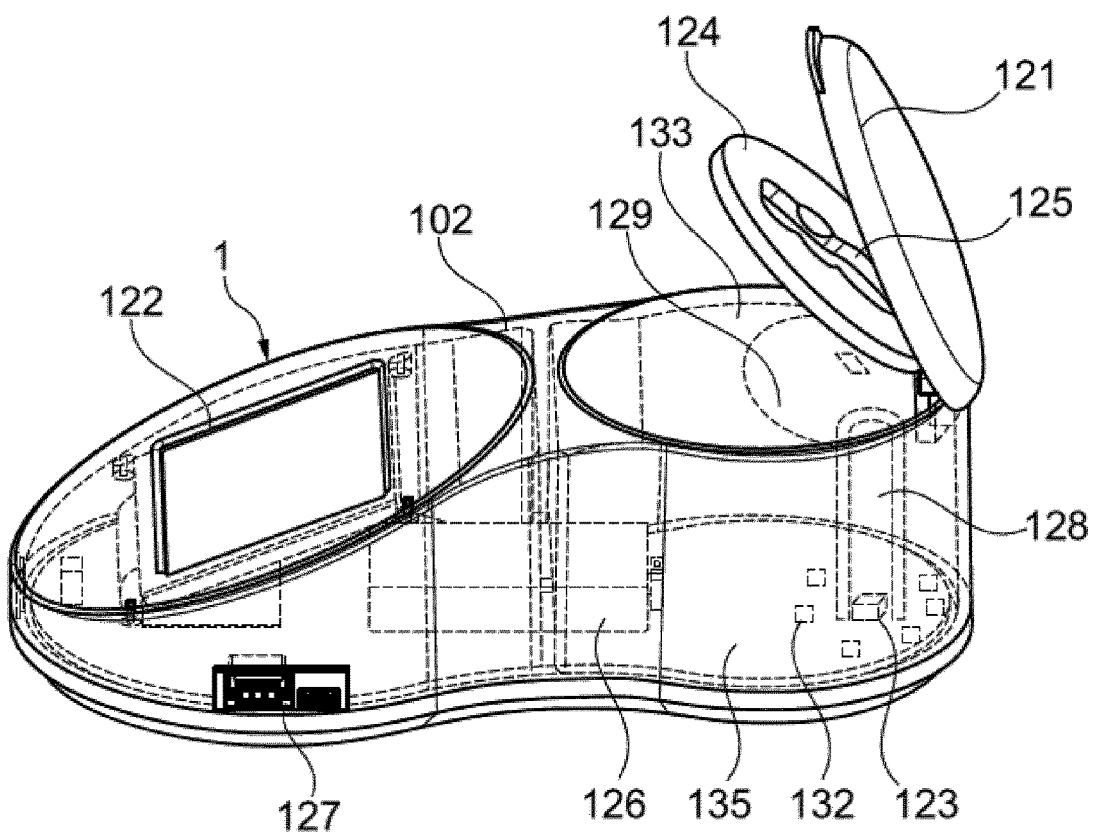
FIG. 2 shows an isometric view of the detector unit of FIG. 1 from a slightly different angle and with a portion of the housing made transparent for showing its interior.

Preferably the detector assembly 23 is arranged with an irregularity 230 (see FIG. 3) to make it asymmetric whereby merely one correct positioning of the detector assembly 23 in the fitting place 125 is possible. Further, the detector unit 1 may optionally be arranged with a separate pivotal locating lid 124 mounted under lid 121, with an opening of a shape that matches the outer contour of the detector assembly 23 to assist in holding it in an exact predetermined position in the fitting place 125. Inside the detector housing 102, as shown in FIG. 2, there is an electronic camera 123 for taking a digital photo of the detection compartment 160 through the transparent window 34 of the bottom member 22 of the detector assembly 23. (see FIG. 4) Preferably, the camera 123 is mounted near the bottom of the housing 102 and directed/positioned to capture a digital image through a camera opening 134 of the housing 102 exactly positioned in relation to the fitting place 125, to capture a desired image of the exposed side of the detector device 160. Lights 132 are provided within the housing 102 to provide a desired illumination of the detector device 160. The detector housing 102 further comprises a CPU 126, a display 122 and generally also at least one USB port 127. The digital photo is transmitted to the CPU 126, which after processing the data passes them on to the display 122. Preferably, a sensor (not shown) senses the closing of the lid 121 and sends a signal to the CPU 126 to start a timer when the lid protrusion 211 activates the detector assembly 23. (It is evident that other means than a lid protrusion may be used for activation, e.g. an electronically activated pushing member that may be activated remotely and/or by a button on the housing 102).

As schematically shown in FIG. 2, in the preferred embodiment the fitting place 125 is arranged in the separate pivotal locating lid 124 that normally rests on a support surface 133 of the housing 102, but which may be lifted, e.g. to enable cleaning. Preferably, the camera 123 is mounted within a tube formed member 128 (schematically shown in cross section) directed towards the camera window 134 for the detector device 160. Adjacent at the top of the tube 128 and surrounding it there may be a diffusor 129. Below the diffusor 129 a plurality of lights 132 are located that lights the diffusor 129, which in turn provides a homogenous light through the camera window 134 onto the detector device 160. Preferably, the camera 123 is mounted near the bottom of the housing 102 within the tube formed member 128, which then preferably extends substantially vertically up to a position near below the camera window 134, i.e. positioned to extend substantially perpendicularly in relation to the exposed side of the detector device 160 of the detector assembly 23. The plurality of lights 132 preferably are LED lights that provide a symmetric illumination of the detector device 160, more preferred at least three LED lights 132 are symmetrically placed outside of and around the periphery of the tube formed member 128, more preferred there are at least four LED lights 132, which are positioned on the bottom 135 of the housing 102. As an alternative to a sensor (not shown) senses the closing of the lid 121 and sends a signal to the CPU 126 to start a timer when the lid protrusion 211 activates the detector assembly 23.

The novel detector assembly 23 of the invention will be explained first with reference to FIGS. 3-7 that show a preferred embodiment of the inventive detector assembly 23 for use in the detection of a biomarker, such as bilirubin, in a sample of a flowable substance. In the following, a presentation of the various components of the detector assembly will first be given and an explanation of how they cooperate with each other will then be given with reference to FIGS. 8-13.

Figure 3:
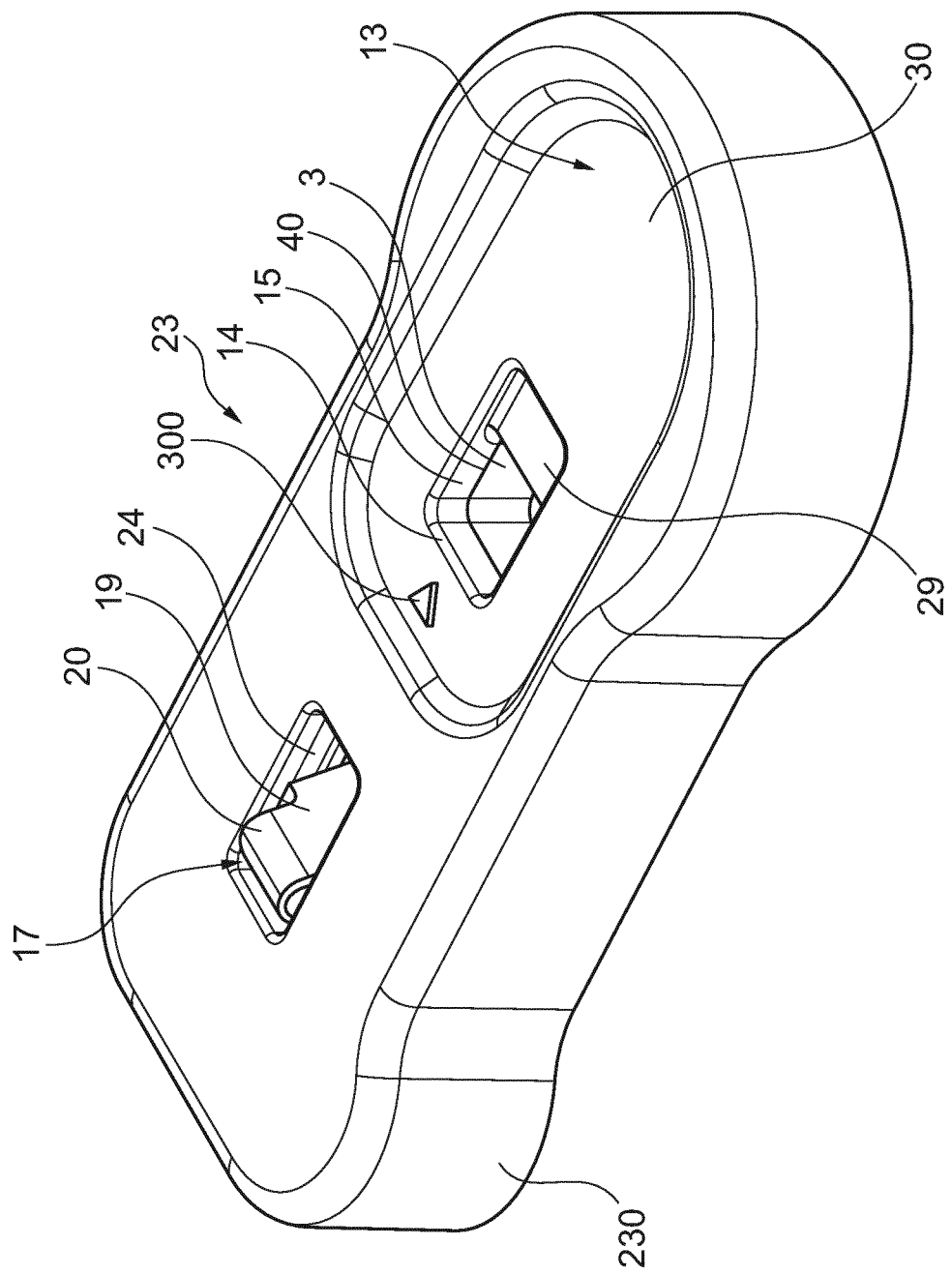
FIG. 3 shows, in perspective, the detector assembly according to the present invention.
Figure 4:
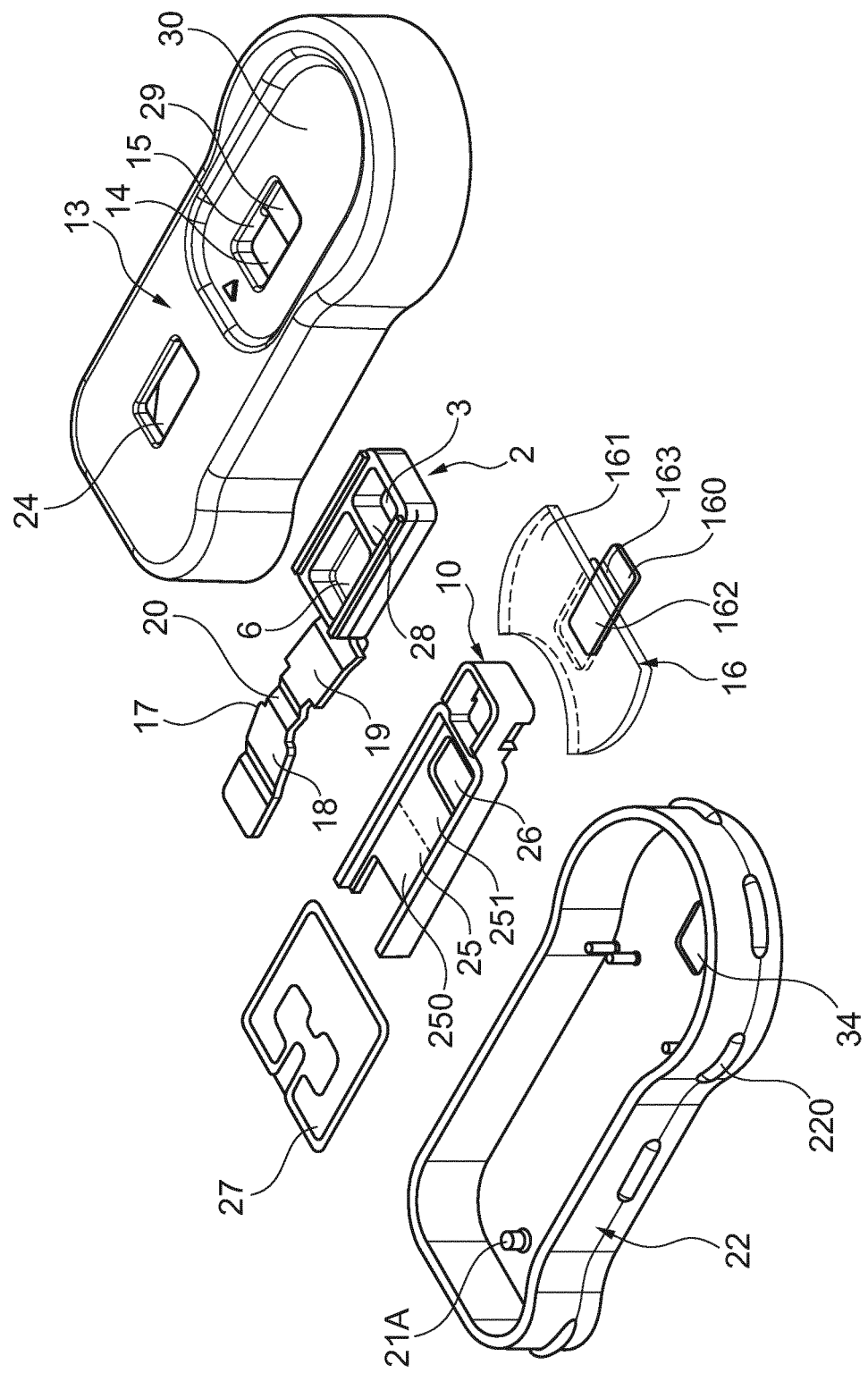
FIG. 4 shows, in perspective, separate parts of the detector assembly when the detector assembly has been disassembled.
Figure 5:
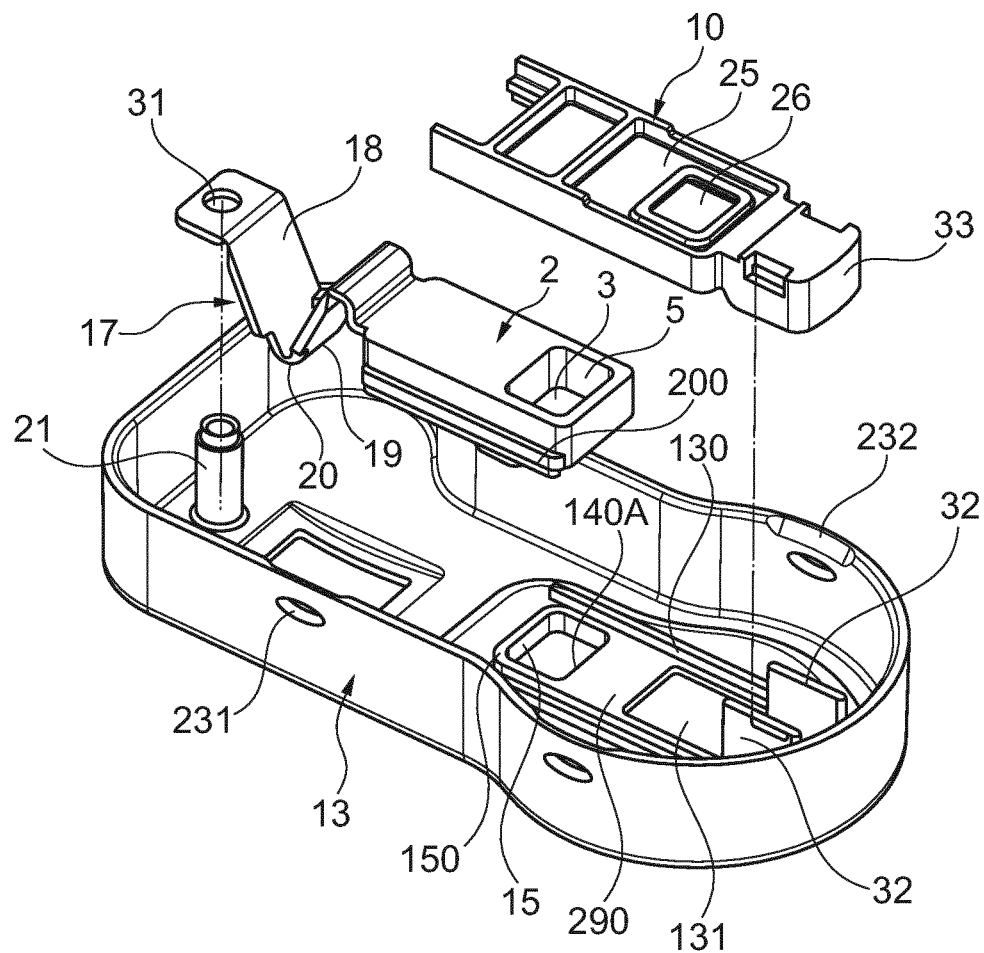
FIG. 5 shows, in perspective and from below, three of the components of the inventive detector assembly.
Figure 6:
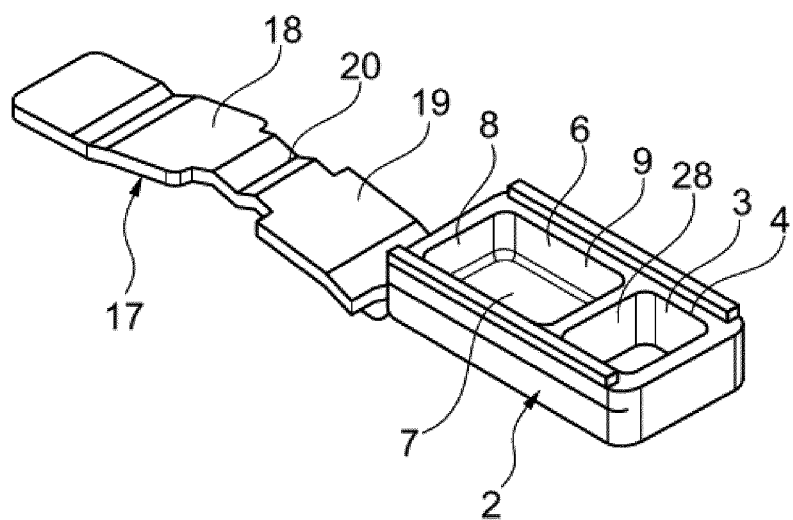
FIG. 6 shows, in perspective and in larger scale, one of the components of FIG. 5.
Figure 7:
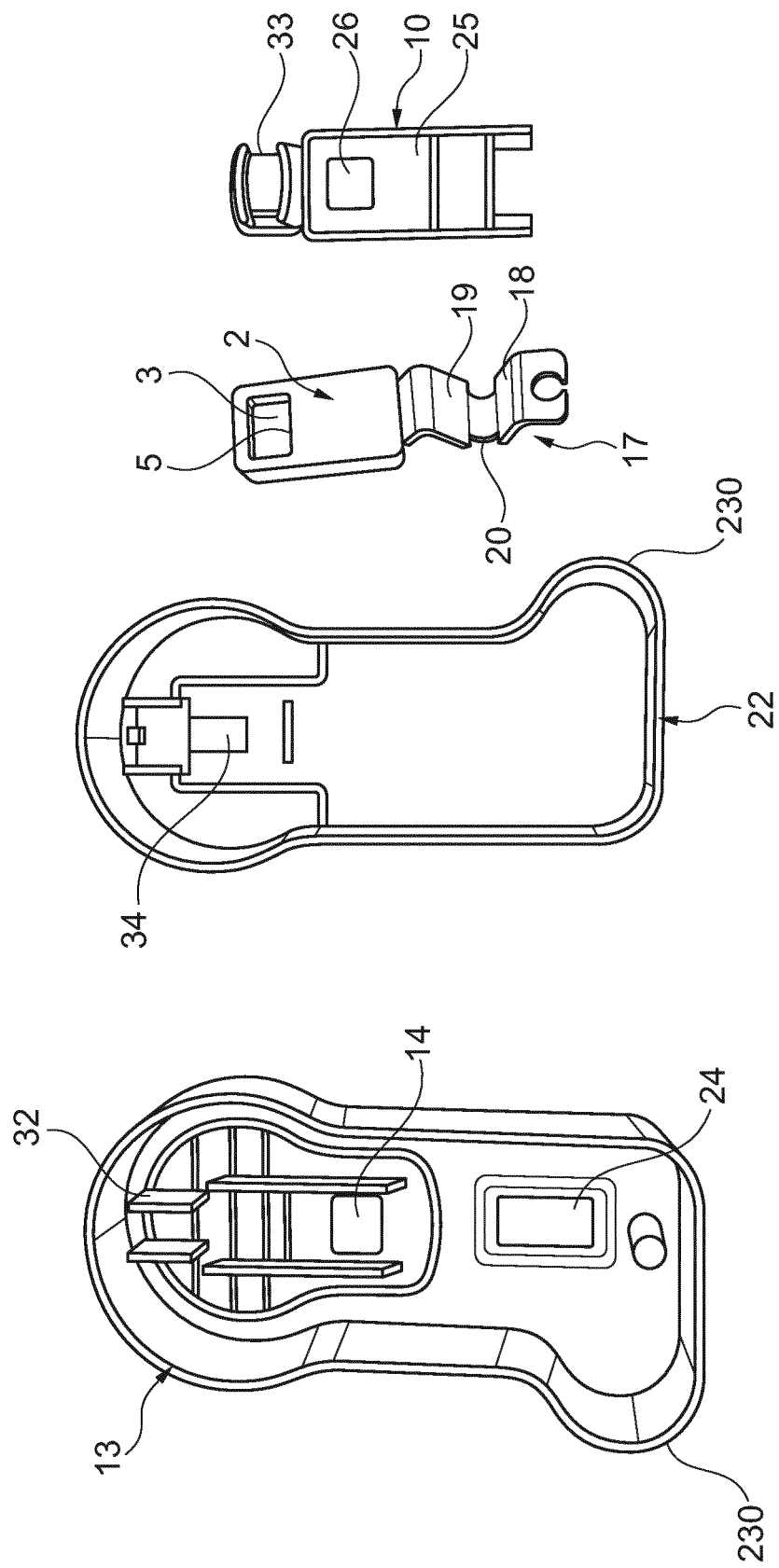
FIG. 7 shows, in perspective, the cover and the bottom part together with the guide, the receiver body and the activation mechanism.
Figure 11:
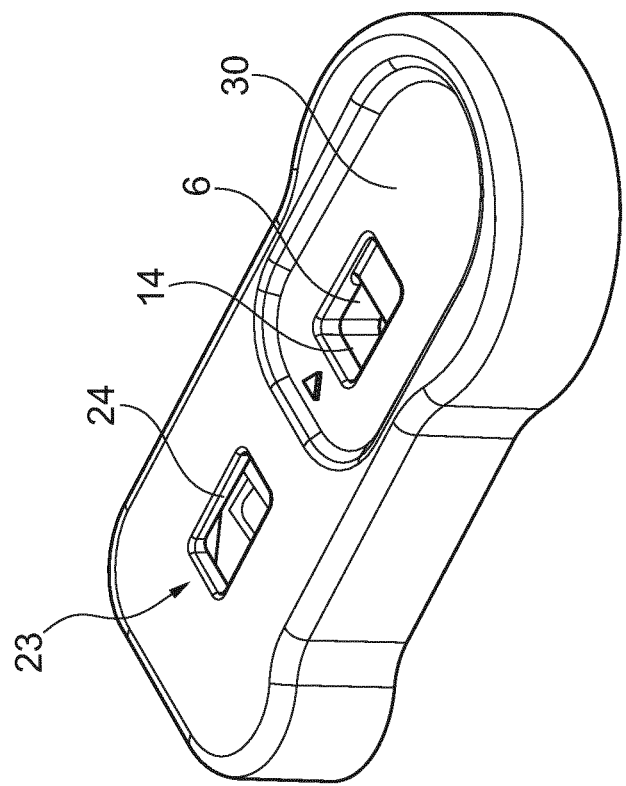
FIG. 11 is a perspective view similar to FIG. 9 illustrating what the detector assembly looks like from outside when the receiver body is in its second position.

FIG. 3 shows the inventive detector assembly 23 in a state ready for use. The detector assembly 23 has a shell which is composed of a cover 13 and a bottom part 22 (FIG. 3 and FIG. 4). With reference to FIG. 4, FIG. 5 and FIG. 6, the detector assembly comprises a receiver body 2 that is shaped to define a receiving chamber 3 into which a flowable substance such as, for example, blood can be supplied. The receiving chamber 3 has an inlet opening 4 through which the flowable substance can enter the receiving chamber 3 and the receiving chamber 3 also has an outlet opening 5 (see FIG. 5) on the opposite side of the receiver body 2. A flowable substance that has been supplied to the receiving chamber can leave the receiving chamber 3 through the outlet opening 5 provided that the outlet opening 5 is not blocked. When the outlet opening 5 is blocked such that flowable substance cannot leave the receiving chamber through the outlet opening 5, the receiving chamber 3 has a maximum capacity for holding a volume of the flowable substance. According to the preferred embodiment of the invention, the sample receiver body 2 is shaped to define an overflow chamber 6 that is separated from the receiving chamber 3 and the overflow chamber 6 has a bottom 7, a circumferential wall 8 and chamber opening 9. The overflow chamber 6 preferably is substantially larger than the receiving chamber 3, providing space for a relatively large amount of excess flowable substance contained above the upper limiting surfaces 40 of the receiving chamber 3, i.e. above the sealing surfaces 150 of the walls 15 of the opening 14 (see FIG. 5), such that all excess flowable substance may be contained in the overflow chamber 6.

The detector assembly 23 also comprises a guide 10 for the receiver body 2 (see FIG. 4 and FIG. 5). The guide 10 is shaped to cooperate with the receiver body 2 such that the receiver body 2 can be caused to move relative to the guide 10 in a movement from a first position in which the outlet opening 5 is blocked to a second position in which the outlet opening 5 is not blocked and the path of the movement is determined by cooperating surfaces of the guide 10 and the receiver body 2. The guide 10 includes a plate 25 having first surface 250 that blocks the outlet 5 of the receiving chamber 3 in the first position and preferably also second surface 251 that blocks the outlet 5 of the receiving chamber 3 in an intermediate position between the first and second positions. The detector assembly 23 also comprises a cover 13 which cover is connected to the guide 10 in such a way that the guide 10 and the cover 13 are in a fixed position relative to each other. In practice, the cover 13 does not have to be directly connected to the guide 10. The cover 13 may conceivably be connected indirectly to the guide 10 in that the guide 10 is connected to another part which in turn is connected to the cover 13. When it is here stated that the guide 10 is connected to the cover 13, that should be understood as meaning that the position of the guide 10 is fixed in relation to the cover 13, either by direct connection or through some other element. The receiver body 2 is in contact with the cover 13 at least when the receiver body 2 is in its first position, and the cover 13 is further shaped to define an opening 14 that can be made to at least partially coincide with the inlet opening 4 of the receiving chamber 3 when the receiver body 2 is in the first position and to coincide with the chamber opening 9 of the overflow chamber 6 when the receiver body 2 is in its second position.

The opening 14 in the cover 13 is limited by a circumferential wall 15 (see FIG. 3 and FIG. 4) that forms an extension of the receiving chamber 3 when the receiver body 2 is in its first position such that the receiving chamber 3 and the opening in the cover 13 can cooperate to hold a quantity of the flowable substance that exceeds the maximum capacity of the receiving chamber 3 itself when the receiver body 2 is in its first position.

The walls 15 defining the extension of the opening 14 terminate in a common plane forming sealing surfaces 150 that is in contact with the upper surfaces 40 that surrounds the inlet opening 4 of the receiver body 2. Within the opening 14 there may be arranged a roof member 29 that preferably is positioned at a lower level than the bottom of the depression 30, forming a kind of thin roof member 29 having an outer edge 29A that coincides with the front wall 300 of the receiving chamber 3. The roof member 29 with its relatively thin edge 29A will arrange for a kind of cutting action of the flowable substance contained in the receiving chamber and in excess above it, i.e. up to the top of the opening 14 and possibly also in the depression 30, such that exactly the desired amount can be contained in the receiving chamber 3 when moved away from the first position. The roof member 29 form part of a sealing upper plate 290, which sealing upper plate 290 has at least the same width and length as the width and length defined by the upper edges of the receiving chamber 3, which will safe guard that the desired volume of flowable substance in the receiving chamber 3 is maintained during transition forward thereof. Further it is shown that in the direction of movement of the receiver body 2, next to the sealing upper plate 290, preferably there is arranged a minor upper depression 131 on the rear side of the depression 30, which upper depression 131 assists in allowing the flowable substance in the receiving chamber 3 to move downwards into the desired detection path, i.e. through the opening 26, in the bottom part 22. Hence, this depression 131 may safeguard that there is no vacuum hindering movement by gravity of the flowable substance downwards.

In a preferred embodiment, as shown in more detail in FIG. 5, the cover 13 at the rear side of the depression 30 is arranged with guide members 130 that may assist in a linear movement of the receiver body 2. The receiver body 2 may be arranged with adapted guide rails 200 cooperating with the guide members 130 of the cover 13. Further the cover 13 may be arranged with connection members 231, 232, 220, preferably in the form of snap in members 232, 220 for easy assembly of the detector assembly 23 and also to provide a desired pinching force attracting the two members 13, 22, which can be used to apply a desired pressure onto the filter/assembly 16, which in the preferred embodiment is achieved by means of the fastening parts 32, i.e. having an adapted height such that the upper ends 32A will exert a desired pressure on the filter/assembly 16.

The receiving chamber 3 and the overflow chamber 6 may be separated from each other by a wall part 28.

An RFID tag 27 may be placed in the detector assembly to handle data related to the detector assembly 23, e.g. kind of biomarker to be tested and/or e.g. implying a specific kind of software/algorithm, batch number (e.g. implying a specific kind of compensation as determined by tests of said batch) production date (e.g. implying possibility to control accepted life), etc, which data may be transferred to the CPU 126 in connection with loading a detector assembly 23 in the fitting place 125 of the detector unit 1. Preferably data from the RFID tag 27 is transferred automatically to the CPU 126 in a first step, i.e. before an actual detection process is started.

The detector device 160 of the detector assembly 23 may be or comprise or be a part of a permeable member 16 such as a filter device 16. Such a filter device 16 may optionally comprise or hold a reagent. The filter device 16 is located in the detector assembly 23 in a position that is adjacent the outlet opening 5 of the receiving chamber 3 when the receiver body 2 is in its second position. However, it should be understood that the inventive detector assembly 16 may have a detector device 160 formed by a filter that is without such a reagent such that it is left to the user of the detector assembly to provide a suitable reagent or no reagent at all. It should also be understood that the detector device 160 need not be a filter device but could take another form. For example, it may be formed by a piece of porous plastic (not shown) that may or may not comprise a reagent.

As used herein, the term "detector device" refers to any object or substance that will be affected by a predefined biomarker in such a way that contact between the detector device and a flowable substance containing the biomarker, such as bilirubin, results in a visible change in the detector device such that observation of the detector device can be used as an indication of the presence of the predefined biomarker, such as bilirubin, in the flowable substance or the lack of such a presence.

The detector device 160 or detector assembly 23 may (or may not) comprise or hold a reagent such as a chemical compound. However, it has advantageously been found that rather surprising the novel concept of the invention may be used to detect and determine the amount of bilirubin without a reagent. When a reagent is used, the reagent is preferably contained within or adjacent a permeable member 16, which more preferred is a filter device 16, whereby the reagent may be positioned in or adjacent to the filter device 16, which reagent shifts color upon presence of a biomarker in the sample of flowable substance. The reagent may have such a reagent composition that it is arranged to react with one or more of the following biochemical markers, all of which may be present in plasma: LDH, Hemoglobin (Hb), aspartate aminotransferase (AST), alanine aminotransferase (ALT), lactate, Creatinine Kinase (CK), Creatinine, Amylasis (PIA), C-reactive protein (CRP), Hydrogen ion concentration (pH), Albumin, K, Mg and Ca. It is to be understood that the examples mentioned above are by no means limiting to the basic principles of the invention.

A filter device 16 (or another permeable member 16) may be a single filter member, for example. However, in the preferred embodiment as shown in FIG. 4 it is a filter assembly 160, 161, 162, 163, e.g. comprising two 161, 162 uppermost separation filters, a plasma transportation filter 163 and a detection filter 160, which is adapted to be located at the "window 34" in the bottom part 22.

For convenience, the reference numeral 160 will be used in the following to refer to the detector device and that a filter device or a filter which is part of a filter assembly 16 may serve as a detector device. However, it should be understood that some other detector device may be used.

It is expected that, in most cases, the flowable substance will be a liquid such as blood, urine, saliva, or semen but this is not necessarily the case.

Embodiments of the invention are conceivable in which a user is expected to move the receiver body by simply pushing directly on the receiver body. However, in preferred embodiments of the invention, the detector assembly 23 comprises an activation mechanism 17 operatively connected to the guide 10 such that pressing the activation mechanism 17 causes the activation mechanism 17 to act on the receiver body 2 to move it along the guide 10 from the first position of the receiver body 2 to the second position of the receiver body 2.

In advantageous embodiments, the detector assembly 23 comprises a bottom part 22, wherein the cover 13 is connected to the bottom part 22 such that the bottom part 22 and the cover 13 together form a shell in which the guide, the receiver body 2 and the activation mechanism 17 are located and wherein the cover 13 is shaped to define an access opening 24 for the activation mechanism 17 such that a user can access the activation mechanism 17 through the access opening 24 and cause the receiver body 2 to move from its first position to its second position. Optionally, the guide 10 may be secured to the bottom part 22 such that the position of the guide 10 is fixed in relation to the bottom part 22. In this way, the guide 10 will be indirectly connected to the cover 13 through the bottom part 22 when the bottom part 22 and the cover are connected to each other.

While an activation mechanism 17 may take many different forms, an advantageous embodiment may be as follows and will be explained with reference to FIG. 5 and FIG. 6. The activation mechanism 17 may comprise a first link 18 and a second link connected 19 to each other by an articulated joint 20. The first link 18 may be secured to a part of the shell 23. In the embodiment illustrated in FIG. 3, the first link 18 may have a through-hole 31 that can cooperate with a peg 21 that is integral with the cover 13 such that the first link 18 is secured on the peg 21. The second link 19 is either connected to the receiver body 2 or in contact with the receiver body 2 such that it can push it. In a preferred embodiment, the activation mechanism 17 is integral the receiver body 2 but embodiments are conceivable in which the activation mechanism 17 is separate from the receiver body 2 but arranged to be able to contact the receiver body 2 and push it. The first link 18 and the second link 19 have such dimensions that the can form a V-shaped protrusion when the receiver body 2 is in its first position and which V-shaped protrusion is accessible through the access opening 24 such that it can be pressed down by an operator thereby causing the articulated joint 20 to move toward the bottom part 22 and the receiver body 2 to move from its first position to its second position.

As mentioned above there is a plate 25 that blocks the outlet opening 5 of the receiving chamber 3 when the receiver body 2 is in its first position (see FIG. 4 and FIG. 5). Preferably, the plate 25 is included in the guide 10 and further comprises an opening 26 that coincides with the outlet opening 5 of the receiving chamber 3 when the receiver body 2 is in its second position such that flowable substance can leave the receiving chamber 3 through that opening 26 via the outlet opening 5 when the receiver body 2 is in its second position.

The bottom part 22 may be made of a transparent material such that it may be visually observed/detected what happens with the detector device 160 when the flowable substance comes into contact with it. Alternatively, a window 34 (see FIG. 4) may be provided in the bottom part 22 through which the detector device may be observed.

The cover 13 may advantageously be provided with fastening parts 32 (see FIG. 5) adapted to cooperate with a head 33, preferably positioned adjacent the opening 26 for the flowable substance, of the guide 10 such that the guide 10 is secured to the cover 13 and also adapted to assist in providing an appropriate pressure onto a filter/assembly 16.

The inventive method, and the function of the inventive detector assembly, will now be explained with reference to FIGS. 8-13.

Figure 10:
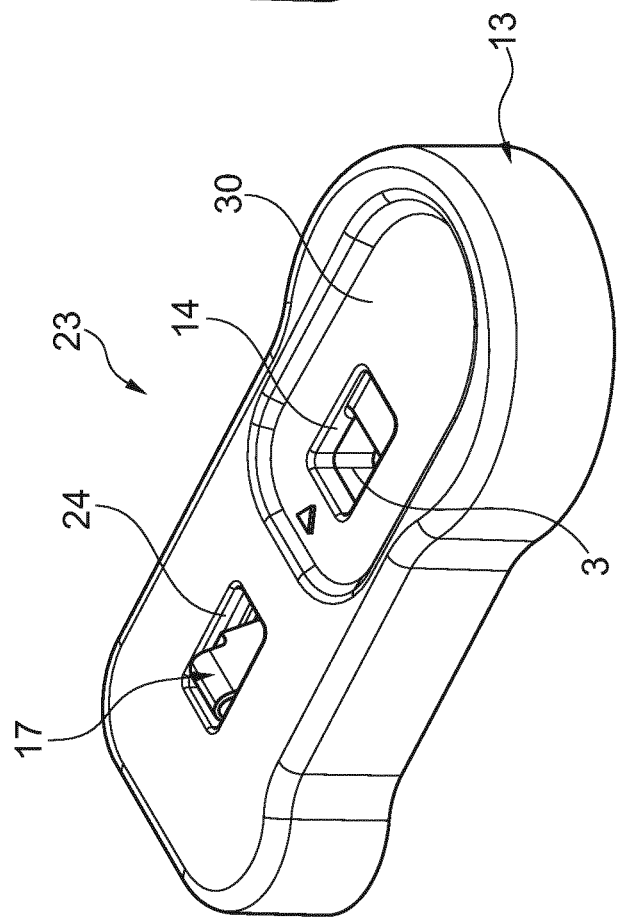
FIG. 10 is a perspective view similar to FIG. 8 illustrating what the detector assembly looks like from outside when the receiver body is in its first position.

Using the inventive detector assembly 23, a detector device 160 such as included in a filter device 16 is provided and placed in the detector assembly 23. A quantity of the flowable substance is supplied to the receiving chamber 3. At this stage, the receiver body 2 is in its first position as can be seen in FIG. 8 and FIG. 10. In this position of the receiver body 2, the inlet opening 4 of the receiving chamber coincides with the opening 14 in the cover 13. The circumferential wall 15 of the opening 14 forms an extension of the receiving chamber 3 such that it is possible to supply flowable substance exceeding the maximum capacity of the receiving chamber 3 itself. The cover 13 may further have a depression 30 surrounding the area around the opening 14 in the cover such that overflow beyond the combined capacity of the receiving chamber 3 and the circumferential wall 15 can be absorbed (to a limit). In this position, the plate 25 of the guide 10 is located below the outlet opening 5 of the receiving chamber and blocks the outlet opening 5 such that the flowable substance cannot leave the receiving chamber 3.

After the flowable substance has been added to the receiving chamber 3, the receiver body 2 is caused to move along the guide 10 from the first position to the second position. This can be done by pressing on the activation mechanism 17 such that the articulated joint 17 is pressed downwards from the position of FIG. 8 to the position of FIG. 9. The second link 19 will then push the receiver body 2 such that it moves to its second position along the guide 10. When the receiver body 2 moves to its second position, excess quantity of the flowable substance will be wiped off/skimmed off by the edge of the opening 14 of the cover 13, i.e. by a part of the circumferential wall 15 of the opening 14. Any quantity of the flowable substance that has been poured into the receiving chamber 3 and which exceeds the maximum capacity of the receiving chamber 3 itself will this be separated from the rest of the flowable substance that has been poured into the receiving chamber 3. Since the receiver body has now moved to its second position, the opening 14 of the cover 13 will now coincide with the opening 9 of the overflow chamber 6 (see FIG. 9) such that excess flowable substance will enter the overflow chamber 6 whereby the quantity of flowable substance which remains in the receiving chamber 3 will be a metered quantity. Since the receiver body 2 has moved to its second position, the plate 25 can no longer block the outlet opening 5 of the receiving chamber 3. In the second position of the receiver body 2, the outlet opening 5 of the receiving chamber 3 coincides with the opening 26 in the plate 25. The flowable substance is thus free to leave the receiving chamber 3 and come into contact with the detector device 160 (e.g. included in a filter assembly 16). Here, it will be understood that the detector device 160 has been placed adjacent the second position of the receiver body, i.e. adjacent the opening 26 in the plate 25 of the guide 6 such that flowable substance that leaves the receiving chamber will come into contact with the detector device 160.

Preferably, the guide 10 and the receiver body 2 are shaped to cooperate with each other in a linear movement but embodiments are conceivable in which the receiver body 2 moves in any other way, for example in an arc Instead of letting the guide 10 be shaped such that a part of it blocks the outlet opening 5 when the receiver body 2 is in its first position, a different element could serve the same function. For example, a part of the bottom part 22 could be designed to block the outlet opening when the receiver body 2 is in its first position.

It should also be understood that movement of the receiver body 2 does not necessarily have to be caused by an activation mechanism 17 as described above. For example, movement of the receiver body 2 from its first position to its second position could conceivably be caused by pushing or pressing directly on the receiver body 2. However, it is preferred that the movement of the receiver body 2 is caused by pressing an activation mechanism 17 operatively connected to the receiver body 2 such that pressing the activation mechanism 17 causes the activation mechanism 17 to act on the receiver body 2 to move it from the first position of the receiver body 2 to the second position of the receiver body 2.

In most practical cases, it would be normal to simply rely on the force of gravity to cause the flowable substance to leave the receiving chamber 3 through the outlet opening 5. However, the flowable substance could conceivably be caused to leave the receiving chamber by other means, for example by applying pressure to the flowable substance.

Thanks to the invention, it is possible to obtain a precisely metered quantity of flowable substance to analyze. The invention also overcomes or reduces the problem arising from surface tension since excess flowable substance is skimmed off.

The activation mechanism of the inventive detector assembly offers an effective way of moving the receiver body when the receiver body is located inside a shell and would otherwise be difficult to access directly. The shell, in turn, protects the receiving chamber and other parts of the detector assembly from being polluted by dirt particles.

While the invention has been described above in terms of a detector assembly and a method of detecting the presence of a biomarker, such as bilirubin, in a sample of a flowable substance, it should be understood that those categories only reflect different aspects of one and the same invention.

It is evident for the skilled person that there are many evident modifications that the skilled person may provide without inventive skill, i.e. within the essential basic principles of the invention. For instance, it is evident that the walls 15 that provide the extended upper volume of the receiving chamber 3 may be provided in various forms. For instance, it is evident that these walls 15 merely can be provided as a homogenous part of the upper wall of the cover 13. An advantageous feature with having wall parts extending downwards and having wall surfaces that substantially coincide with the inner surfaces of the receiving chamber, is that excess amount of flowable substance may always be reliably obtained in combination with providing an appropriate sealing function, i.e. that an advantageous interface between the upper level of the flowable substance in the receiving chamber 3 and the upper part 13 of the detector assembly 23 may be achieved. Furthermore it is foreseen that the guide member 10 may be an integral part of one or more members forming the detector assembly 23 and furthermore that the guide member 10 may also be formed by several separate parts wherein assembly of the separate parts may be achieved in different ways, to obtain the basic functionality of having a guide member 10 that guides movement of the receiving chamber 3 and also directly or indirectly assist in maintaining the desired amount of flowable substance within the receiving chamber 3 when moving from the first to the second position. Likewise, the plate like part 29 that partly assists in separating the predetermined amount within the receiving chamber 3 from the excess amount and that partly assists in retaining the desired amount within the receiving chamber 3 during the transport from the first position to the second position, may also be achieved in various manners by integral and/or separate parts being fixated in different and various manners. Furthermore, it is evident that the excess of flowable substance may be collected in various manners within the detector assembly 23, i.e. in various manners departing from the use of a container device 6 that moves along with the receiver body 2, which may be advantageous due to the fact that it is thereby relatively easy to have control of the collected excess of flowable substance, e.g. thereby avoiding undesired spillage. However, it is foreseen that the excess fluid may be retained in a containing member forming a part of the detector assembly 23 as such, e.g. an adapted chamber within the bottom part 22 that may be flowably divided from the portion of the detection assembly containing the detector, e.g. by means of an appropriate dividing wall member, e.g. attached to the receiver body. Moreover, it is foreseen that the essential features of the method according to the invention may be applied without having the receiving chamber 3 provided in a detector assembly 23, i.e. having the basic functionality of the method incorporated in a detector unit wherein at least some of the parts described above as belonging to a detector assembly 23 may form parts of the detector unit.

FIRST LIST OF EXAMPLES

1. A method of detecting the presence of a biomarker in a sample of a flowable substance, the method comprising: providing a receiver body (2) shaped to define a receiving chamber (3) having an inlet opening (4) through which the flowable substance can enter the receiving chamber (3) and the receiving chamber (3) further having an outlet opening (5) through which a flowable substance can leave the receiving chamber (3) when the outlet opening (5) is not blocked, the receiving chamber (3) having a maximum capacity for holding a volume of the flowable substance when the outlet opening (5) is blocked; providing a detector device (160); and supplying a quantity of the flowable substance to the receiving chamber (3) and causing it to pass through the outlet opening and come into contact with the detector, characterised in that, in that a guide (10) for the receiver body (2) is provided which guide (10) is shaped to cooperate with the receiver body (2) such that the receiver body (2) can be caused to move relative to the guide (10) in a movement from a first position in which the outlet opening (5) is blocked to a second position in which the outlet opening (5) is not blocked, wherein preferably the path of which movement is determined by cooperating surfaces of the guide (10) and the receiver body (2); in that a cover (13) is provided which cover is connected to the guide (10) in such a way that the guide (10) and the cover (13) are in predefined, preferably fixed, positions relative to each other, wherein the receiver body (2) is in contact with the cover (13) at least when the receiver body (2) is in its first position, and which cover (13) is further shaped to define an opening (14) that can be made to at least partially coincide with the inlet opening (4) of the receiving chamber (3) when the receiver body (2) is in the first position and which opening (14) in the cover (13) is limited by a circumferential wall (15) that forms an extension of the receiving chamber (3) when the receiver body (2) is in its first position such that the receiving chamber (3) and the opening in the cover (13) can cooperate to hold a quantity of the flowable substance that exceeds the maximum capacity of the receiving chamber (3) itself when the receiver body (2) is in its first position; in that the detector device (160) is placed in a position which is adjacent the outlet opening (5) of the receiving chamber (3) when the receiver body (2) is in its second position such that flowable substance can leave the receiving chamber (3) and come into contact with the detector device (160); and in that the method further comprising delivering a quantity of the flowable substance into the receiving chamber (3) while the receiver body (2) is in its first position and subsequently causing the receiver body (2) to move along the guide (10) from the first position to the second position such that any quantity of the flowable substance that has been delivered to the receiving chamber (3) and which exceeds the maximum capacity of the receiving chamber (3) itself will be separated from the rest of the flowable substance that has been delivered to the receiving chamber (3) and instead enter an overflow chamber (6) whereby the quantity of flowable substance which remains in the receiving chamber (3) will be a metered quantity that is free to leave the receiving chamber (3) and come into contact with the detector device (160), wherein receiver body (2) is provided within a detector assembly (23) and the detector assembly (23) comprises members (25,29) having surfaces (251, 290) that block the outlet (5) and the inlet (4) respectively in the path of travel of the receiver body (2) between the first position and the second position.

2. A method according to example 1, wherein the overflow chamber (6) forms a part of the sample receiver body (2) that is separated from the receiving chamber (3) and wherein preferably the overflow chamber (6) has a bottom (7), a circumferential wall (8) and chamber opening (9), and wherein the opening (14) of the cover (13) is arranged to at least partly coincide with the chamber opening (9) of the overflow chamber (6) when the receiver body (2) is in its second position and/or is being moved from its first to its second position.

3. A method according to example 1 or example 2, wherein gravity is used to cause the flowable substance to leave the receiving chamber (3) through the outlet opening (5) and wherein the guide (10) is shaped such that the guide blocks the outlet opening (5) of the receiving chamber (3) when the receiver body (2) is in its first position.
4. A method according to any examples 1-3, wherein the movement of the receiver body (2) is caused by pushing or pressing directly on the receiver body (2), and preferably that the movement of the receiver body (2) is a linear movement.
5. A method according to any of examples 1-4, wherein movement of the receiver body (2) is caused by pressing an activation mechanism (17) operatively connected to the receiver body (2) such that pressing the activation mechanism (17) causes the activation mechanism (17) to act on the receiver body (2) to move it from the first position of the receiver body (2) to the second position of the receiver body (2).
6. A method according to any of the preceding examples, wherein the detector device (160) is arranged in a detector assembly (23) having a window (34) enabling taking a digital photo of an exposed surface of the detector device (160).
7. A detector assembly (23) for use in the detection of a biomarker in a sample of a flowable substance, the detector assembly (23) comprising: a receiver body (2) shaped to define a receiving chamber (3) having an inlet opening (4) through which the flowable substance can enter the receiving chamber (3) and the receiving chamber (3) further a having an outlet opening (5) through which a flowable substance can leave the receiving chamber (3) when the outlet opening (5) is not blocked; and a detector (16) which is located in the detector assembly (23), the receiving chamber (3) having a maximum capacity for holding a volume of the flowable substance when the outlet opening (5) is blocked, characterised in that that the detector assembly (23) comprises a guide (10) for the receiver body (2) which guide (10) is shaped to cooperate with the receiver body (2) such that the receiver body (2) can be caused to move relative to the guide (10) in a movement from a first position in which the outlet opening (5) is blocked to a second position in which the outlet opening (5) is not blocked, the path of which movement is determined by cooperating surfaces of the guide (10) and the receiver body (2); in that the detector assembly (23) comprises a cover (13) which cover is connected to the guide (10) in such a way that the guide (10) and the cover (13) are in predefined, preferably fixed, positions relative to each other, wherein the receiver body (2) is in contact with the cover (13) at least when the receiver body (2) is in its first position, and which cover (13) is further shaped to define an opening (14) that can be made to at least partially coincide with the inlet opening (4) of the receiving chamber (3) when the receiver body (2) is in the first position and which opening (14) in the cover (13) is limited by a circumferential wall (15) that forms an extension of the receiving chamber (3) when the receiver body (2) is in its first position such that the receiving chamber (3) and the opening in the cover (13) can cooperate to hold a quantity of the flowable substance that exceeds the maximum capacity of the receiving chamber (3) itself when the receiver body (2) is in its first position, and in that the detector (16) is located in the detector assembly (23) in a position that is adjacent the outlet opening (5) of the receiving chamber (3) when the receiver body (2) is in its second position, wherein the detector assembly (23) comprises members (25,29) having surfaces (251, 290) that block the outlet (5) and the inlet (4), respectively, in the path of travel of the receiver body (2) between the first position and the second position.
8. A detector assembly (23) according to example 7, comprising an overflow chamber (6), wherein preferably the overflow chamber (6) forms a part of the sample receiver body (2) that is separated from the receiving chamber (3) and wherein more preferred the overflow chamber (6) has a bottom (7), a circumferential wall (8) and chamber opening (9), which chamber opening (9) is arranged to coincide with the opening (14) of the cover (13) when the receiver body (2) is in its second position and/or is being moved from its first to its second position.
9. A detector assembly (23) according to example 7, wherein the detector (16) further comprises or holds a reagent.
10. A detector assembly (23) according to any of examples 7-9, wherein the detector assembly (23) comprises an activation mechanism (17) operatively connected to the guide (10) such that pressing the activation mechanism (17) causes the activation mechanism (17) to act on the receiver body (2) to move it along the guide (10) from the first position of the receiver body (2) to the second position of the receiver body (2).
11. A detector assembly (23) according to any of examples 7-10, wherein the detector assembly (23) comprises a bottom part (22) in which the guide (10) is secured such that the position of the guide (10) is fixed in relation to the bottom part (22), wherein the cover (13) is connected to the bottom part (22) such that the bottom part (22) and the cover (13) together form a shell (23) in which the guide, the receiver body (2) and the activation mechanism (17) are located and wherein the cover (13) is shaped to define an access opening (24) for the activation mechanism (17) such that a user can access the activation mechanism (17) through the access opening (24) and cause the receiver body (2) to move from its first position to its second position.
12. A detector assembly (23) according to example 11, wherein the activation mechanism (17) comprises a first link (18) and a second link connected (19) to each other by an articulated joint (20), the first link (18) being secured to a part (21) of the shell (23) and the second link (19) being connected to the receiver body (2), the first (18) and the second link (19) having such dimensions that they can form a V-shaped protrusion when the receiver body (2) is in its first position and which V-shaped protrusion is accessible through the access opening (24) such that it can be pressed down by an operator thereby causing the articulated joint (20) to move toward the bottom part (22) and the receiver body (2) to move from its first position to its second position.
13. A detector assembly (23) according to any of examples 7-12, wherein the guide (10) comprises a plate (25) that blocks the outlet opening (5) of the receiving chamber (3) when the receiver body (2) is in its first position, but which has an opening (26) that coincides with the outlet opening (5) of the receiving chamber (3) when the receiver body (2) is in its second position such that flowable substance can leave the receiving chamber (3) through the outlet opening (5) when the receiver body (2) is in its second position.

14. A detector unit (1) for use in detection of the presence of a biomarker in a sample of a flowable substance, said unit (1) including a portable detector housing (102) having a CPU (126), a display (122) and a fitting place (125) for reception of a detector assembly (23) having a detector device (160), preferably according to any of examples 7-12, adapted to be located in said fitting place (125) and said detector housing (102) comprising an electronic camera (123) and lights (132) for taking a digital photo of the detector device (160) through a window (34) of the detector assembly (23), wherein the detector housing (102) includes a shielding member (128) arranged to shield the camera (123) from undesired light and a diffusor (135) arranged to provide illumination from said lights (132) onto said detector device (160), wherein the detector housing (102) comprises an activation device (211) arranged to activate the detector assembly (23), and said activation device (211) is movably arranged in relation to said fitting place (125) to push the activation mechanism of the detector assembly (23) upon simultaneously triggering a detection process within the detector unit.

15. A detector unit (1) according to example 14, wherein said detector assembly (23) is arranged with an irregularity (230) of its outer configuration and said fitting place (125) being adapted to said outer configuration to thereby safeguard correct positioning of the detector assembly (23) in the fitting place (125).

16. A detector unit (1) according to any of examples 14-15, wherein the shielding member (128) is a tube formed member (128) enclosing the camera (123) directed/positioned towards a camera opening (134) of the detector housing (102).

17. A detector unit (1) according to any of examples 14-16, wherein a plurality of LED lights is arranged to provide a symmetric illumination of the detector device (160) via the diffusor (129).

SECOND LIST OF EXAMPLES

1. A method of detecting the presence of a bilirubin in a sample of a flowable substance, the method comprising: providing a receiver body (2) shaped to define a receiving chamber (3) having an inlet opening (4) through which the flowable substance can enter the receiving chamber (3) and the receiving chamber (3) further having an outlet opening (5) through which a flowable substance can leave the receiving chamber (3) when the outlet opening (5) is not blocked, the receiving chamber (3) having a maximum capacity for holding a volume of the flowable substance when the outlet opening (5) is blocked; providing a detector device (160); and supplying a quantity of the flowable substance to the receiving chamber (3) and causing it to pass through the outlet opening and come into contact with the detector, characterised in that, in that a guide (10) for the receiver body (2) is provided which guide (10) is shaped to cooperate with the receiver body (2) such that the receiver body (2) can be caused to move relative to the guide (10) in a movement from a first position in which the outlet opening (5) is blocked to a second position in which the outlet opening (5) is not blocked, wherein preferably the path of which movement is determined by cooperating surfaces of the guide (10) and the receiver body (2); in that a cover (13) is provided which cover is connected to the guide (10) in such a way that the guide (10) and the cover (13) are in predefined, preferably fixed, positions relative to each other, wherein the receiver body (2) is in contact with the cover (13) at least when the receiver body (2) is in its first position, and which cover (13) is further shaped to define an opening (14) that can be made to at least partially coincide with the inlet opening (4) of the receiving chamber (3) when the receiver body (2) is in the first position and which opening (14) in the cover (13) is limited by a circumferential wall (15) that forms an extension of the receiving chamber (3) when the receiver body (2) is in its first position such that the receiving chamber (3) and the opening in the cover (13) can cooperate to hold a quantity of the flowable substance that exceeds the maximum capacity of the receiving chamber (3) itself when the receiver body (2) is in its first position; in that the detector device (160) is placed in a position which is adjacent the outlet opening (5) of the receiving chamber (3) when the receiver body (2) is in its second position such that flowable substance can leave the receiving chamber (3) and come into contact with the detector device (160); and in that the method further comprising delivering a quantity of the flowable substance into the receiving chamber (3) while the receiver body (2) is in its first position and subsequently causing the receiver body (2) to move along the guide (10) from the first position to the second position such that any quantity of the flowable substance that has been delivered to the receiving chamber (3) and which exceeds the maximum capacity of the receiving chamber (3) itself will be separated from the rest of the flowable substance that has been delivered to the receiving chamber (3) and instead enter an overflow chamber (6) whereby the quantity of flowable substance which remains in the receiving chamber (3) will be a metered quantity that is free to leave the receiving chamber (3) and come into contact with the detector device (160), and further by detecting the amount of bilirubin by optical analysis of the color of an exposed of said detector device (160), wherein receiver body (2) is provided within a detector assembly (23) and the detector assembly (23) comprising members (25,29) having surfaces (251, 290) that block the outlet (5) and the inlet (4) respectively in the path of travel of the receiver body (2) between the first position and second positions.

2. A method according to example 1, wherein the overflow chamber (6) forms a part of the sample receiver body (2) that is separated from the receiving chamber (3) and wherein preferably the overflow chamber (6) has a bottom (7), a circumferential wall (8) and chamber opening (9), and wherein the opening (14) of the cover (13) is arranged to at least partly coincide with the chamber opening (9) of the overflow chamber (6) when the receiver body (2) is in its second position and/or is being moved from its first to its second position, wherein preferably gravity is used to cause the flowable substance to leave the receiving chamber (3) through the outlet opening (5) and wherein the guide (10) is shaped such that the guide blocks the outlet opening (5) of the receiving chamber (3) when the receiver body (2) is in its first position.

3. A method according to any of examples 1-2, wherein movement of the receiver body (2) is caused by pressing an activation mechanism (17) operatively connected to the receiver body (2) such that pressing the activation mechanism (17) causes the activation mechanism (17) to act on the receiver body (2) to move it from the first position of the receiver body (2) to the second position of the receiver body (2).

4. A method according to any of the preceding examples, wherein the detector device (160) is arranged in a detector assembly (23) having a window (34) enabling taking a digital photo of the of an exposed surface of the detector device (160).

5. A detector assembly (23) for use in the detection of a bilirubin in a sample of a flowable substance, the detector assembly (23) comprising: a receiver body (2) shaped to define a receiving chamber (3) having an inlet opening (4) through which the flowable substance can enter the receiving chamber (3) and the receiving chamber (3) further a having an outlet opening (5) through which a flowable substance can leave the receiving chamber (3) when the outlet opening (5) is not blocked; and a detector (16) which is located in the detector assembly (23), the receiving chamber (3) having a maximum capacity for holding a volume of the flowable substance when the outlet opening (5) is blocked, characterised in that that the detector assembly (23) comprises a guide (10) for the receiver body (2) which guide (10) is shaped to cooperate with the receiver body (2) such that the receiver body (2) can be caused to move relative to the guide (10) in a movement from a first position in which the outlet opening (5) is blocked to a second position in which the outlet opening (5) is not blocked, the path of which movement is determined by cooperating surfaces of the guide (10) and the receiver body (2); in that the detector assembly (23) comprises a cover (13) which cover is connected to the guide (10) in such a way that the guide (10) and the cover (13) are in predefined, preferably fixed, positions relative to each other, wherein the receiver body (2) is in contact with the cover (13) at least when the receiver body (2) is in its first position, and which cover (13) is further shaped to define an opening (14) that can be made to at least partially coincide with the inlet opening (4) of the receiving chamber (3) when the receiver body (2) is in the first position and which opening (14) in the cover (13) is limited by a circumferential wall (15) that forms an extension of the receiving chamber (3) when the receiver body (2) is in its first position such that the receiving chamber (3) and the opening in the cover (13) can cooperate to hold a quantity of the flowable substance that exceeds the maximum capacity of the receiving chamber (3) itself when the receiver body (2) is in its first position, and in that the detector device (160) is located in the detector assembly (23) in a position that is adjacent the outlet opening (5) of the receiving chamber (3) when the receiver body (2) is in its second position, wherein the detector assembly (23) comprises members (25,29) having surfaces (251, 290) that block the outlet (5) and the inlet (4) respectively in the path of travel of the receiver body (2) between the first position and second positions.

6. A detector assembly (23) according to example 5, wherein the detector assembly (23) comprises an activation mechanism (17) operatively connected to the guide (10) such that pressing the activation mechanism (17) causes the activation mechanism (17) to act on the receiver body (2) to move it along the guide (10) from the first position of the receiver body (2) to the second position of the receiver body (2).

7. A detector unit (1) for use in detection of the presence of a bilirubin in a sample of a flowable substance, said unit (1) including a portable detector housing (102) having a CPU (126), a display (122) and a fitting place (125) for reception of a detector assembly (23) having a detector device (160), preferably according to any of examples 7-12, adapted to be located in said fitting place (125) and said detector housing (102) comprising an electronic camera (123) and lights (132) for taking a digital photo of the detector device (160) through a window (34) of the detector assembly (23), wherein the detector housing (102) includes a shielding member (128) arranged to shield the camera (123) from undesired light and a diffusor (135) arranged to provide illumination from said lights (132) onto said detector device (160), wherein the detector housing (102) comprises an activation device (211) arranged to activate the detector assembly (23), and said activation device (211) is movably arranged in relation to said fitting place (125) to push the activation mechanism of the detector assembly (23) upon simultaneously triggering a detection process within the detector unit, 8. A detector unit (1) according to the preceding example, wherein said detector assembly (23) is arranged with an irregularity (230) of its outer configuration and said fitting place (125) being adapted to said outer configuration to thereby safeguard correct positioning of the detector assembly (23) in the fitting place (125), and more preferred the shielding member (128) is a tube formed member (128) enclosing the camera (123) directed/positioned towards a camera opening (134) of the detector housing (102) and preferably also wherein a plurality of LED lights are arranged to provide a symmetric illumination of the detector device (160) via the diffusor (129).

The invention claimed is:

1. A method of detecting the presence of a biomarker in a sample of a flowable substance, the method comprising:

providing a receiver body shaped to define a receiving chamber having an inlet opening through which the flowable substance can enter the receiving chamber and the receiving chamber further having an outlet opening through which a flowable substance can leave the receiving chamber when the outlet opening is not blocked, the receiving chamber having a maximum capacity for holding a volume of the flowable substance when the outlet opening is blocked;

providing a detector device; and supplying a quantity of the flowable substance to the receiving chamber and causing it to pass through the outlet opening and come into contact with the detector, wherein:

a guide for the receiver body is provided, which guide is shaped to cooperate with the receiver body such that the receiver body is configured to move relative to the guide in a movement from a first position in which the outlet opening is blocked to a second position in which the outlet opening is not blocked, wherein the path of which movement is determined by cooperating surfaces of the guide and the receiver body;

a cover is provided, which cover is connected to the guide in such a way that the guide and the cover are in predefined, preferably fixed, positions relative to each other, the receiver body is in contact with the cover at least when the receiver body is in its first position, and which cover is further shaped to define an opening that can be made to at least partially coincide with the inlet opening of the receiving chamber when the receiver body is in the first position and which opening in the cover is limited by a circumferential wall that forms an extension of the receiving chamber when the receiver body is in its first position such that the receiving chamber and the opening in the cover can cooperate to hold a quantity of the flowable substance that exceeds the maximum capacity of the receiving chamber itself when the receiver body is in its first position;

the detector device is placed in a position which is adjacent the outlet opening of the receiving chamber when the receiver body is in its second position such that flowable substance can leave the receiving chamber and come into contact with the detector device; and the method further comprises delivering a quantity of the flowable substance into the receiving chamber while the receiver body is in its first position and subsequently causing the receiver body to move along the guide from the first position to the second position such that any quantity of the flowable substance that has been delivered to the receiving chamber and which exceeds the maximum capacity of the receiving chamber itself will be separated from the rest of the flowable substance that has been delivered to the receiving chamber and instead enter an overflow chamber whereby the quantity of flowable substance which remains in the receiving chamber will be a metered quantity that is free to leave the receiving chamber and come into contact with the detector device, wherein the receiver body is provided within a detector assembly and the detector assembly comprises members having surfaces that block the outlet and the inlet respectively in the path of travel of the receiver body between the first position and the second position.

2. The method according to claim 1, wherein the overflow chamber forms a part of the sample receiver body that is separated from the receiving chamber and wherein preferably the overflow chamber has a bottom, a circumferential wall and chamber opening, and wherein the opening of the cover is arranged to at least partly coincide with the chamber opening of the overflow chamber when the receiver body is in its second position and/or is being moved from its first to its second position.

3. The method according to claim 1, wherein gravity is used to cause the flowable substance to leave the receiving chamber through the outlet opening and wherein the guide is shaped such that the guide blocks the outlet opening of the receiving chamber when the receiver body is in its first position.

4. The method according to claim 1, wherein the movement of the receiver body is caused by pushing or pressing directly on the receiver body, and preferably that the movement of the receiver body is a linear movement.

5. The method according to claim 1, wherein movement of the receiver body is caused by pressing an activation mechanism operatively connected to the receiver body such that pressing the activation mechanism causes the activation mechanism to act on the receiver body to move it from the first position of the receiver body to the second position of the receiver body.

6. The method according to claim 1, wherein the detector device is arranged in a detector assembly having a window enabling taking a digital photo of an exposed surface of the detector device.

7. The method according to claim 1, wherein the biomarker is bilirubin.

8. A detector assembly for use in the detection of a biomarker in a sample of a flowable substance, the detector assembly comprising:

a receiver body shaped to define a receiving chamber having an inlet opening through which the flowable substance can enter the receiving chamber and the receiving chamber further a having an outlet opening through which a flowable substance can leave the receiving chamber when the outlet opening is not blocked;

a detector, which is located in the detector assembly, the receiving chamber having a maximum capacity for holding a volume of the flowable substance when the outlet opening is blocked;

a guide for the receiver body, which guide is shaped to cooperate with the receiver body such that the receiver body is configured to move relative to the guide in a movement from a first position in which the outlet opening is blocked to a second position in which the outlet opening is not blocked, the path of which movement is determined by cooperating surfaces of the guide and the receiver body; and a cover which cover is connected to the guide in such a way that the guide and the cover are in predefined, preferably fixed, positions relative to each other, wherein the receiver body is in contact with the cover at least when the receiver body is in its first position, and which cover is further shaped to define an opening that can be made to at least partially coincide with the inlet opening of the receiving chamber when the receiver body is in the first position and which opening in the cover is limited by a circumferential wall that forms an extension of the receiving chamber when the receiver body is in its first position such that the receiving chamber and the opening in the cover can cooperate to hold a quantity of the flowable substance that exceeds the maximum capacity of the receiving chamber itself when the receiver body is in its first position, wherein: the detector is located in the detector assembly in a position that is adjacent the outlet opening of the receiving chamber when the receiver body is in its second position, the detector assembly further comprises members having surfaces configured to block the outlet and the inlet, respectively, in the path of travel of the receiver body between the first position and the second position.

9. The detector assembly according to claim 8, comprising an overflow chamber, wherein preferably the overflow chamber forms a part of the sample receiver body that is separated from the receiving chamber and wherein more preferred the overflow chamber has a bottom, a circumferential wall and chamber opening, which chamber opening is arranged to coincide with the opening of the cover when the receiver body is in its second position and/or is being moved from its first to its second position.

10. The detector assembly according to claim 8, wherein the detector further comprises or holds a reagent.

11. The detector assembly according to claim 8, wherein the detector assembly comprises an activation mechanism operatively connected to the guide such that pressing the activation mechanism causes the activation mechanism to act on the receiver body to move it along the guide from the first position of the receiver body to the second position of the receiver body.

12. The detector assembly according to claim 8, wherein the detector assembly comprises a bottom part in which the guide is secured such that the position of the guide is fixed in relation to the bottom part, wherein the cover is connected to the bottom part such that the bottom part and the cover together form a shell in which the guide, the receiver body and the activation mechanism are located and wherein the cover is shaped to define an access opening for the activation mechanism such that a user can access the activation mechanism through the access opening and cause the receiver body to move from its first position to its second position.

13. The detector assembly according to claim 12, wherein the activation mechanism comprises a first link and a second link connected to each other by an articulated joint, the first link being secured to a part of the shell and the second link being connected to the receiver body, the first and the second link having such dimensions that they can form a V-shaped protrusion when the receiver body is in its first position and which V-shaped protrusion is accessible through the access opening such that it can be pressed down by an operator thereby causing the articulated joint to move toward the bottom part and the receiver body to move from its first position to its second position.

14. The detector assembly according to claim 8, wherein the guide comprises a plate that blocks the outlet opening of the receiving chamber when the receiver body is in its first position, but which has an opening that coincides with the outlet opening of the receiving chamber when the receiver body is in its second position such that flowable substance can leave the receiving chamber through the outlet opening when the receiver body is in its second position.

15. The detector assembly according to claim 8, wherein the biomarker is bilirubin.

16. A detector unit for use in detection of the presence of a biomarker in a sample of a flowable substance, said unit comprising:
a portable detector housing having a CPU,
a display, and
a fitting place for reception of a detector assembly having a detector device, according to claim 8, configured be located in said fitting place, wherein:
said detector housing comprises an electronic camera and lights for taking a digital photo of the detector device through a window of the detector assembly,
the detector housing comprises a shielding member configured to shield the camera from undesired light and a diffusor configured to provide illumination from said lights onto said detector device,
detector housing comprises an activation device configured to activate the detector assembly, and
said activation device is movably arranged in relation to said fitting place configured to push the activation mechanism of the detector assembly upon simultaneously triggering a detection process within the detector unit.

17. The detector unit according to claim 16, wherein said detector assembly is arranged with an irregularity of its outer configuration and said fitting place being adapted to said outer configuration to thereby safeguard correct positioning of the detector assembly in the fitting place.

18. The detector unit according to claim 16, wherein the shielding member is a tube formed member enclosing the camera directed/positioned towards a camera opening of the detector housing.

19. The detector unit according to claim 16, wherein a plurality of LED lights is arranged to provide a symmetric illumination of the detector device via the diffusor.

20. The detector unit according to claim 16, wherein the biomarker is bilirubin.

* * * * *

UNITED STATES PATENT AND TRADEMARK OFFICE
CERTIFICATE OF CORRECTION

| | | |
|---|---|---|
| PATENT NO. | : 11,906,531 B2 | Page 1 of 1 |
| APPLICATION NO. | : 17/254609 | |
| DATED | : February 20, 2024 | |
| INVENTOR(S) | : Anna Söderlund et al. | |

It is certified that error appears in the above-identified patent and that said Letters Patent is hereby corrected as shown below:

On the Title Page

On Page 2, in Column 1, item (57), Line 7, delete "receive body (2)" and insert -- receiver body (2) --, therefor.

In the Claims

In Column 22, Line 4, Claim 8, delete "further a having" and insert -- further having --, therefor.

In Column 24, Line 2, Claim 16, delete "configured be" and insert -- configured to be --, therefor.

Signed and Sealed this
Eleventh Day of June, 2024

Katherine Kelly Vidal
*Director of the United States Patent and Trademark Office*